(12) United States Patent
Zebda et al.

(10) Patent No.: US 11,469,433 B2
(45) Date of Patent: Oct. 11, 2022

(54) THERMO-ELECTRIC GENERATOR, ASSOCIATED IMPLANTABLE DEVICE AND METHOD

(71) Applicants: UNIVERSITE GRENOBLE ALPES, Saint Martin d'Heres (FR); INSTITUT NATIONAL DE LA SANTE ET DE LA RECHERCHE MEDICALE (INSERM), Paris (FR); CENTRE HOSPITALIER UNIVERSITAIRE GRENOBLE ALPES, La Tronche (FR)

(72) Inventors: Abdelkader Zebda, Grenoble (FR); Philippe Cinquin, Saint Nazaire les Eymes (FR); Jean-Pierre Alcaraz, Pontcharra (FR); Donald Martin, Gieres (FR); Aziz Bakri, Grenoble (FR); Nawel Khalef, Meylan (FR)

(73) Assignees: UNIVERSITE GRENOBLE ALPES, Saint Martin d'Heres (FR); INSTITUT NATIONAL DE LA SANTE ET DE LA RECHERCHE MEDICALE (INSERM), Paris (FR); CENTRE HOSPITALIER RÉGIONAL DE GRENOBLE, La Tronche (FR)

( * ) Notice: Subject to any disclaimer, the term of this patent is extended or adjusted under 35 U.S.C. 154(b) by 140 days.

(21) Appl. No.: 17/058,521

(22) PCT Filed: May 23, 2019

(86) PCT No.: PCT/EP2019/063381
§ 371 (c)(1),
(2) Date: Nov. 24, 2020

(87) PCT Pub. No.: WO2019/224325
PCT Pub. Date: Nov. 28, 2019

(65) Prior Publication Data
US 2021/0196962 A1 Jul. 1, 2021

(30) Foreign Application Priority Data

May 24, 2018 (FR) .................................. 1854398

(51) Int. Cl.
*H01M 8/16* (2006.01)
*A61N 1/378* (2006.01)
(Continued)

(52) U.S. Cl.
CPC ............ *H01M 8/16* (2013.01); *A61N 1/3785* (2013.01); *H01L 35/02* (2013.01); *H01L 35/30* (2013.01);
(Continued)

(58) Field of Classification Search
CPC ... A61B 5/14532; A61B 5/1486; H01L 35/02; H01L 35/30; H01M 8/16; H01M 4/86; A61N 1/3785
See application file for complete search history.

(56) References Cited

U.S. PATENT DOCUMENTS

| 6,131,581 A | 10/2000 | Leysieffer et al. |
| 2005/0038483 A1 | 2/2005 | MacDonald |
| 2015/0054468 A1 | 2/2015 | Nikonov et al. |

FOREIGN PATENT DOCUMENTS

| DE | 10 2006 027 350 | 12/2007 |
| EP | 2 124 267 | 11/2009 |
| WO | 2006/017226 | 2/2006 |

OTHER PUBLICATIONS

Achraf Ben Amar, et al., "Power Approaches for Implantable Medical Devices", Sensors, vol. 15, No. 11, Nov. 13, 2015, p. 28889-28914 (26 pages).
(Continued)

*Primary Examiner* — Mayla Gonzalez Ramos
(74) *Attorney, Agent, or Firm* — Nixon & Vanderhye

(57) ABSTRACT

Thermo-electric generator which is intended to be immersed in a fluid which contains at least one chemical species,
(Continued)

comprising two electrodes each having a first end and a second end, the first ends being connected to each other, the generator being configured to generate an electrical voltage between the two ends when a temperature difference is imposed between each first end and the corresponding second end, the temperature difference being such that one end, referred to as the "hot end", of each electrode has a temperature which is strictly greater than the temperature of the other end. The hot end of at least one electrode comprises a micro-organism or an enzyme which is capable of causing at least one exothermic reaction involving the chemical species.

19 Claims, 3 Drawing Sheets

(51) Int. Cl.
  *H01L 35/02* (2006.01)
  *H01L 35/30* (2006.01)
  *A61N 1/362* (2006.01)
  *H01M 4/86* (2006.01)
(52) U.S. Cl.
  CPC ............... *A61N 1/362* (2013.01); *H01M 4/86* (2013.01); *H01M 2250/00* (2013.01)

(56) References Cited

OTHER PUBLICATIONS

Michael J. Muehlbauer, et al., "Thermoelectric Enzyme Sensor for Measuring Blood Glucose", Biosensors & Bioelectronics, ElSevier Science Ltd., vol. 5, No. 1, Jan. 1, 1990, 12 pages.
Search Report and Written Opinion for FR Application No. 1854398 dated Jan. 31, 2019, 12 pages.
International Search Report for PCT/EP2019/063381 dated Jul. 12, 2019, 7 pages.
Written Opinion of the ISA for PCT/EP2019/063381 dated Jul. 12, 2019, 7 pages.

THERMO-ELECTRIC GENERATOR, ASSOCIATED IMPLANTABLE DEVICE AND METHOD

This application is the U.S. national phase of International Application No. PCT/EP2019/063381 filed May 23, 2019 which designated the U.S. and claims priority to FR Patent Application No. 1854398 filed May 24, 2018, the entire contents of each of which are hereby incorporated by reference.

The present invention relates to a thermo-electric generator. The present invention also relates to an associated method for generating a potential difference.

Devices are used in a large number of applications to generate an electric current or electric voltage to power specific devices or to retrieve energy contained in the environment in which they are placed. However, these devices are generally adapted to certain particular applications and unadapted to others.

For example, biocells catalysing redox reactions between chemical species of the human body have been proposed to power implanted devices such as pacemakers. However, these biocells are only suitable for use in environments having available oxidants and reducing agents able to react together.

In other fields, thermo-electric generators are used to generate an electric current from temperature differences between two zones. For example, such generators allow the recovery of part of the thermal energy derived from some processes via partial conversion thereof to electrical energy.

Generally speaking, thermo-electric generators comprise two electrodes each having a first end and a second end. Each electrode is formed of a doped semiconductor material, the type of doping differing from one electrode to the other. The first ends are electrically connected to each other. When a temperature difference is imposed between the first end and the second end of each electrode, an electric potential difference occurs between the two electrodes, thereby allowing the generation of an electric current. Therefore, when one of the ends is in contact with a hot object such as an exhaust outlet of an industrial installation, and the other end of each electrode is in contact with a cold object, such as an outer wall of the same installation or an expanse of water, part of the thermal energy contained in the exhaust is recovered.

However, the electric power delivered by thermo-electric generators is dependent on the difference in temperature between the first and second ends. The lower this temperature difference, the weaker the delivered electric power. Thermo-electric generators are therefore little adapted for applications in which available temperature differences are low.

There is therefore a need for an electric generator that is adapted to a greater number of applications than prior art generators.

For this purpose, there is proposed a thermo-electric generator intended to be immersed in a fluid containing at least one first chemical species, the thermo-electric generator comprising at least two electrodes, each electrode having a first end and a second end, the first ends being electrically connected to each other, the generator being configured to generate an electric potential difference between the two second ends when a temperature difference is imposed between each first end and the second end of the same electrode, the temperature difference being such that one end called "hot end" among the first end and the second end of each electrode has a temperature strictly greater than the temperature of the other end called "cold end" among the first end and the second end of the same electrode. The hot end of at least one electrode comprises at least one element selected from the group formed by a microorganism and an enzyme, the element being capable of causing at least one exothermic reaction involving the first chemical species.

According to particular embodiments, the thermo-electric generator comprises one or more of the following characteristics, taken alone or in any technically possible combination:

the generator comprises a casing delimiting a chamber housing the two hot ends, the chamber also housing the element, the casing being configured so that at least the first chemical species is able to pass therethrough;

the casing is formed of a porous material, the generator comprises a pump able to inject a stream of fluid from outside the casing to inside the chamber, the casing is formed of a polymer material;

the porous material is composed of a porous 3D matrix;

the 3D porous matrix is fabricated by 3D printing from a viscous paste of a powder of metal particles and a viscous binder;

the size of the pores of the 3D matrix varies from 50 µm up to 1 mm;

the particles of the metal particle powder are: carbon particles, carbon nanotube particles, activated carbon particles, graphene particles, aluminium particles;

the viscous binder is one or a mixture of several elements from among the following compounds: cellulose derivatives, alginate, agarose, polyvinyl alcohol, polyvinyl chloride;

the geometric shape of the matrix is one from among a cube, a cylinder, a slab;

one surface of the matrix is closed by a thermal insulator, the other surfaces of the matrix being closed by a heat-conducting material;

the heat-conducting material is aluminium for example;

the thermal insulator is parylene for example;

the matrix has a fluid inlet and a fluid outlet;

the 3D matrix comprises microorganisms forming a biofilm inside the 3D matrix;

the microorganisms are mixed with a viscous paste of metal particle powder and a viscous binder;

the composite formed by the microorganisms mixed with a viscous paste of metal particle powder and a viscous binder is used to fabricate a porous 3D matrix via 3D printing;

70% to 80% of the surface of the 3D matrix is coated with a thermal insulation layer;

the thermal insulation layer is PCB for example;

the porous matrix is a metal block e.g. aluminium, carbon, titanium, gold or equivalent, the metal block being fabricated by 3D printing;

the generator comprises a block in contact with the hot end of at least one electrode, the block comprising a matrix, the matrix being formed in particular of a polymer material, the element being in the form of particles encapsulated in the matrix;

the element is in the form of compacted particles forming a porous solid;

the element is capable of causing a first exothermic reaction and a second exothermic reaction, the first reaction generating at least one product by reaction of the first chemical species, the second reaction being a reaction involving the product of the first reaction;

at least one element is a microorganism, at least one of the following properties being verified;
   the microorganism comprises a yeast; and
   the microorganism comprises a bacterium.
   the first chemical species is selected from the group formed by: urea, an alcohol and a sugar;
   at least one species is glucose.

The use of a porous 3D matrix advantageously allows an increase in the number or density of the microorganisms through the creation of bacterial or microorganism biofilms on the surface of and inside the porous 3D matrix.

The density of microorganisms is indeed greater in a biofilm than when the microorganisms are in solution.

The porosity of the 3D matrix also advantageously allows feeding of the microorganisms with water and substrates.

The material forming the porous 3D matrix preferably has low specific heat and high heat conduction, which is the case for example with metal and composites thereof, to minimise heat losses in the thermo-electric generator of the invention and thereby optimise the heat released by the microorganisms.

There is also proposed an implantable device configured to be implanted in a human or animal body, comprising a thermo-electric generator such as previously defined, in which the fluid is a body fluid of the human body, the first chemical species particularly being glucose.

According to particular embodiments, the implantable device comprises one or more of the following characteristics, taken alone or in any technically possible combination:
   at least one element comprises an enzyme, the element comprising a glucose oxidase and a catalase;
   the implantable device is a pacemaker.

There is additionally proposed a method for generating an electric potential difference, comprising steps of:
   providing a thermo-electric generator comprising at least two electrodes, each electrode having a first end and a second end, the first ends being electrically connected to each other, the generator being configured to generate an electric potential difference between the two second ends when a temperature difference is imposed between each first end and the second end of the same electrode, the temperature difference being such that one end called "hot end" among the first end and the second end of each electrode has a temperature strictly greater than the temperature of the other end called "cold end" among the first end and the second end of the same electrode, the hot end of at least one electrode comprising at least one element selected from the group formed by a microorganism and an enzyme;
   immersing the thermo-electric generator in a fluid comprising at least one first chemical species;
   implementing, by the element, at least one exothermic reaction involving the first chemical species;
   onset of a temperature difference between the hot end and the cold end of the electrode comprising the element; and
   onset of an electric potential difference between the two second ends.

Characteristics and advantages of the invention will become clearly apparent on reading the following description given solely as a nonlimiting example and with reference to the appended drawings in which:

FIG. 1 schematically illustrates an example of an implantable device comprising a thermo-electric generator of the invention;

Figure 1:
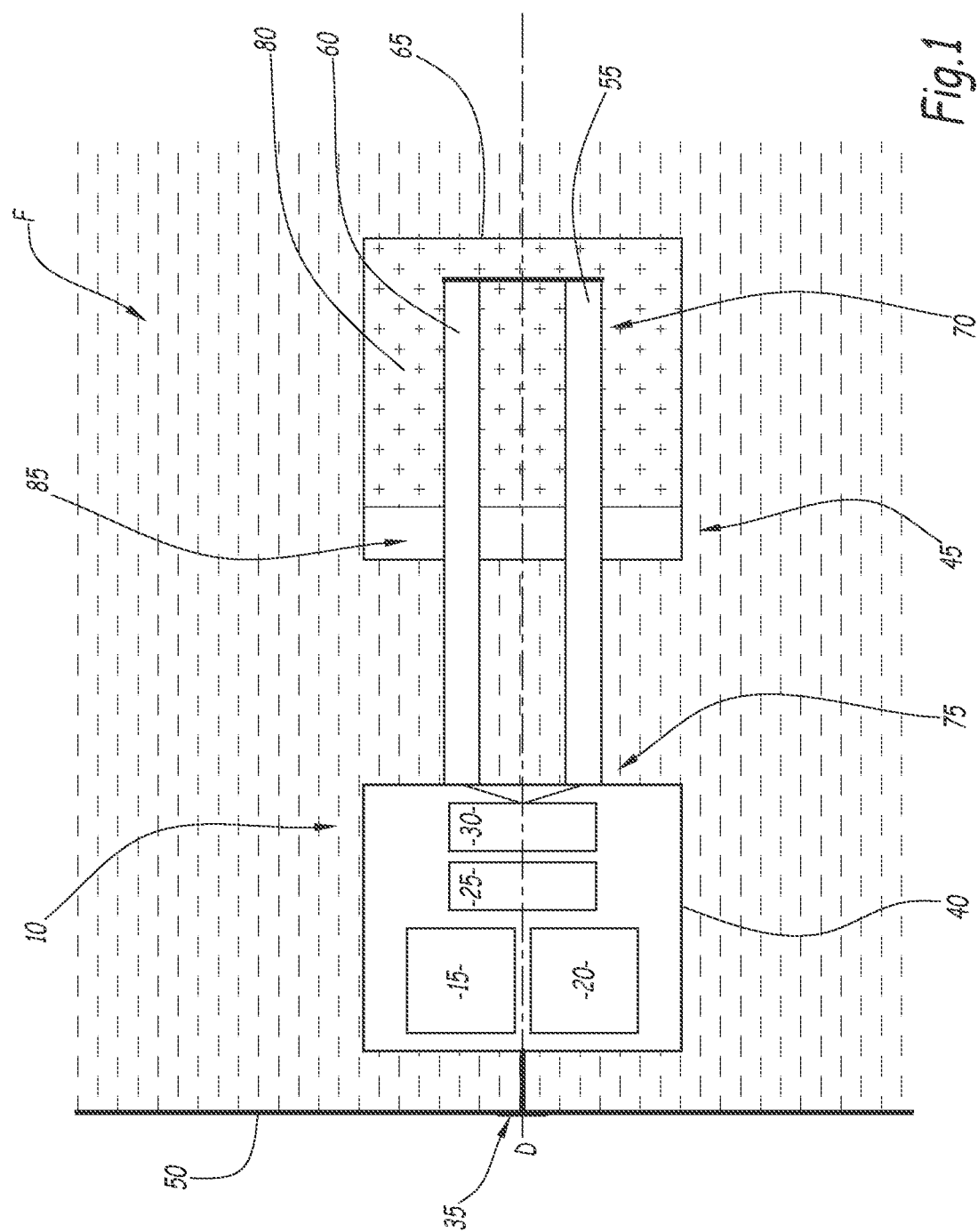

An implantable device 10 is shown in FIG. 1.

By implantable device 10, it is meant that the implantable device 10 is intended to be implanted in the body of an animal e.g. a human being. In particular, by "implantable", it is meant that the implantable device 10 is intended to reside in the body for a time strictly longer than one week, preferably strictly longer than one month, preferably longer than or equal to one year.

For example, the implantable device 10 is configured to be placed in a body cavity of the body containing a fluid F. The intestine or stomach are examples of body cavities.

As a variant, the implantable device 10 is configured to be implanted outside a body cavity, for example in a muscle or under the patient's skin.

The implantable device 10 is configured to stimulate an organ of the body. For example, the organ is the heart and the implantable device 10 is then a pacemaker.

It is to be noted that implantable devices 10 fulfilling functions other than stimulation can also be contemplated. For example, an implantable device 10 comprising a sensor able to measure values of a physiological parameter of the body, such as the level of a specific marker in the body fluid F, and to transmit the measured values to another device can be contemplated.

It can also be contemplated that the implantable device 10 comprises a reserve of active substance such as a medicinal product and is designed to inject the active substance into the body.

Generally speaking, the implantable device 10 is able to fulfil any function requiring the electric powering of the implantable device 10.

For example, the implantable device 10 comprises a stimulation device 15, a controller 20, a storage cell 25, a converter 30, an anchor 35, a first casing 40 and a thermo-electric generator 45.

The fluid F is a body fluid, fully or partially filling the body cavity.

For example, the fluid F is a liquid.

For example, the fluid F is blood. As a variant, the fluid F is peritoneal fluid. In another variant, the fluid F is the liquid contained in the stomach, in particular a mixture of gastric juices.

Extracellular liquid or the fluid contained in the patient's intestine are other examples of fluid F.

The fluid F contains at least one first chemical species C1. In one particular embodiment, the fluid F contains the first chemical species C1 and at least one second chemical species C2.

The first chemical species C1 is a chemical species naturally present in fluid F.

The first chemical species C1 is glucose for example.

It is to be noted that a large number of chemical species are able to fulfil the role of first chemical species C1. Evidently, these include chemical species likely to be present in the fluid in contact with or in the environment of the device. For example, the first species C1 can be selected from the group formed by pyruvate, ascorbic acid, urea, an alcohol and a sugar. Glucose has been mentioned but the other monosaccharides can be added, such as fructose, galactose and mannose (derived from the digestion of carbohydrates or sugars, and/or from food intake) or also glycogen. In another particular embodiment, the sugar is sucrose (in particular if the device is in the stomach).

If the fluid F is extracellular fluid, for example when the implantable device 10 is intended to be implanted under the patient's skin, the first chemical species C1 is glucose for example or pyruvate.

The second chemical species C2 is a chemical species naturally contained in the fluid F.

For example, the second chemical species C2 is dioxygen.

It is to be noted that the first and second chemical species C1 and C2 can be selected from among all the species naturally present in the fluid F. In one embodiment, at least one from among the first chemical species C1 and the second chemical species C2 is an organic molecule derived from food diet and/or derived from the digestion or conversion of foods, and contained the patient's stomach and/or intestine.

In some applications, the first and/or second chemical species C1, C2 can be species naturally present in a biomass e.g. species released upon decomposition of the biomass.

The stimulation device 15 is configured to stimulate the organ.

For example, the stimulation device 15 is configured for electrical stimulation of the organ. In particular, the stimulation device 15 comprises an electrode able to be electrically connected to the organ and is configured to impose an electric voltage between the electrode and the first casing 40.

As a variant, the stimulation device 15 is configured for mechanical stimulation of the organ.

The controller 20 is configured to request stimulation of the organ by the stimulation device 15. For example, the controller 20 is able to compute a stimulation frequency or to detect a physiological phenomenon of the body such as a heart rate anomaly and to request stimulation when the anomaly is detected.

For example, the controller 20 is a data processing unit comprising a memory and a processor.

It is to be noted that other types of controller 20 are able to be used. For example, in one variant, the controller 20 is a programmable logic component. A programmable logic component, also called programmable logic circuit or programmable logic array, is a logic integrated circuit which can be reprogrammed after manufacture. In another variant, the controller 20 is an Application-Specific Integrated Circuit (ASIC). An ASIC is a specialised integrated circuit dedicated to a specific application.

The storage cell 25 is configured to store electrical energy. The storage cell 25 is a supercapacitor for example, or a set of batteries.

The converter 30 is configured to receive a first electric voltage from the thermo-electric generator 45 and in response to generate a second electric voltage powering the storage cell 25, the controller 20 and the stimulation device 15.

The anchor 35 is configured to hold the implantable device 10 in position when the implantable device 10 is implanted in the body. For example, the anchor 35 is configured to be secured to a wall 50 of the body such as a stomach wall.

It is to be noted that numerous types of anchors 35 can be used.

Numerous sites can be contemplated to secure the anchor 35 and the implantable device 10.

The first casing 40 is configured to isolate the stimulation device 15, the controller 20, storage cell 25 and converter 30 from the exterior of the first casing 40, and in particular from the fluid F.

The thermo-electric generator 45 is intended to be immersed in the fluid F. In particular, the thermo-electric generator 45 is intended to be at least partly in contact with the fluid F.

The thermo-electric generator 45 is configured to generate the first electric potential difference. For example, the thermo-electric generator 45 is configured to generate the first electric potential difference and to power the converter 30 with the first electric potential difference.

The thermo-electric generator 45 comprises a first electrode 55, second electrode 60 and a second casing 65.

Each electrode 55, 60 has a first end 70 and a second end 75.

For example, each electrode 55, 60 extends along a main direction D between the first end 70 and the second end 75.

In one embodiment, each electrode 55, 60 has a cross-section of rectangular shape in a plane perpendicular to the main direction D. It is to be noted that the shape of the cross-section may vary from one embodiment to another.

Each electrode 55, 60 is formed of semiconductor material.

By "semiconductor material", it is meant a material having a gap value strictly greater than zero and lower than or equal to 6.5 eV.

By "gap value" of a material, it is meant the value of the bandgap between the valence band and conduction band in the material. The gap value of a material is expressed for example in electron-volts (eV).

The valence band is defined, among the energy bands permitted for an electron in the material under consideration, as being the band having the highest energy whilst being completely filled at a temperature lower than or equal to 20 K.

A first energy level is defined for each valence band. The first energy level is the highest energy level of the valence band.

The conduction band is defined, among the energy bands permitted for an electron in the material, as being the band having the lowest energy whilst being non-filled at a temperature lower than or equal to 20 K.

A second energy level is defined for each conduction band. The second energy level is the lowest energy level of the conduction band.

Therefore, each gap value is measured between the first energy level and the second energy level of the material under consideration.

For example, each electrode 55, 60 is formed of a single semiconductor material.

In one embodiment, at least one electrode 55, 60 comprises a plurality of portions, each portion being formed of a semiconductor material differing from the other portions of the electrode 55, 60 under consideration.

For example, each semiconductor material is selected from the group formed by: an alloy of tellurium and one other element, and a thermoelectric polymer.

When the semiconductor material is an alloy of tellurium and one other element, the other element is bismuth or antimony for example.

It is to be noted that other semiconductor materials may be used.

Polyaniline and polypyrrole are examples of thermoelectric polymers, however other thermoelectric polymers can be contemplated.

The portions are electrically connected together. In particular, the portions are connected in series between the first end 70 and the second end 75. For example, the portions of one same electrode 55, 60 are aligned along the main direction D.

Each second end 75 is electrically connected for example to the converter 30.

For each electrode 55, 60, there is defined a hot end and a cold end.

Each of the hot and cold ends is selected from among the first end 70 and second end 75.

The hot end and cold end are defined by the fact that the thermo-electric generator 45 is configured to generate the first electric potential difference when a temperature difference is imposed between the hot end and the cold end of each electrode 55, 60, the temperature of the hot end being strictly greater than the temperature of the cold end.

In the example illustrated in FIG. 1, the hot end of each electrode 55, 60 is the first end 70, and the cold end of each electrode 55, 60 is the second end 75.

It is to be noted that embodiments in which the cold end of each electrode 55, 60 is the first end 70, and the hot end of each electrode 55, 60 is the second end 75, can also be contemplated.

The first end 70 of each electrode 55, 60 is electrically connected to the first end 70 of the other electrode 55, 60.

The first ends 70 are for example electrically connected to each other via a metal conductor, for example a conductor made of gold, copper or another metal material.

The first electrode 55 has doping of first type. For example, each portion of the first electrode has the first type of doping.

Doping is defined as the presence in a material of impurities contributing free charge carriers. For example, the impurities are atoms of an element which is not naturally contained in the material.

When the presence of impurities increases the volume density of holes in the material compared with the non-doped material, doping is p-type.

When the presence of impurities increases the volume density of free electrons in the material compared with the non-doped material, doping is of n-type.

The first type of doping is selected from among n-type doping and p-type doping. For example, the first type of doping is n-type doping.

The second electrode 60 has doping of a second type selected from among p-type doping and n-type doping. In particular, the second type of doping differs from the first type of doping. For example, the second type of doping is p-type doping.

The hot end of at least one electrode 55, 60 comprises an element 80. For example, the hot end of each electrode 55, 60 comprises an element 80.

On the contrary, the cold end of each electrode 55, 60 is devoid of element 80.

In one embodiment, the thermo-electric generator 45 comprises a single element 80 common to all the electrodes 55, 60.

The element 80 is configured to generate a temperature difference between the first end 70 of the corresponding electrode 55, 60 and the second end 75 of the same electrode 55, 60. In particular, the element 80 is configured to generate a temperature difference such that the temperature of the hot end is strictly greater than the temperature of the cold end.

In particular, the element 80 is capable of causing at least one exothermic reaction involving the first chemical species C1.

In one embodiment, the element 80 is capable of causing at least one first exothermic reaction and at least one second exothermic reaction.

It is to be noted that the number of exothermic reactions caused by the element 80 may vary. For example, embodiments in which the element 80 is capable of causing a single first exothermic reaction can be contemplated, as can embodiments in which the element 80 is capable of causing three or more exothermic reactions.

In one embodiment, each element 80 is a catalyst of the exothermic reaction(s) that the element 80 is capable of generating. A catalyst is a substance which causes a chemical reaction or increases the speed of a chemical reaction without being consumed by this chemical reaction.

Each element 80 is selected from a group formed by a microorganism and an enzyme. For example, the element 80 is an enzyme, a mixture of several enzymes, a microorganism, a mixture of several microorganisms or a mixture of at least one enzyme and at least one microorganism.

An enzyme is a protein having catalytic properties.

In one embodiment, the element 80 is an enzyme. For example, the element 80 is a mixture of two different enzymes. In particular, the element 80 comprises a glucose oxidase and a catalase.

The glucose oxidase (also designated by the acronyms GOx and GOD) is an oxidoreductase enzyme of EC nomenclature EC 1.1.3.4, which catalyses oxidation of glucose to hydrogen peroxide and gluconic acid.

EC nomenclature (EC being the logo of the Enzyme Commission) is a numerical classification of enzymes based on the chemical reaction which they catalyse.

A catalase (from the Greek kataluein "to dissolve") is a heme-containing oxidoreductase which catalyses disproportionation of hydrogen peroxide to water and dioxygen.

Disproportionation is a parallel reaction whereby a chemical species acts both as oxidant and as reducing agent. Disproportionation of hydrogen peroxide to water and dioxygen is defined by the balanced equation:

$$2H_2O_2 \rightarrow O_2 + 2H_2O \qquad \text{(Equation 1)}$$

In one variant, the enzyme comprises at least one enzyme selected from among a sucrase, fructose oxidase and galactose oxidase. For example, the enzyme comprises a glucose oxidase, a catalase, a fructose oxidase, a sucrase and a galactose oxidase.

By "microorganism", it is meant a group of living organisms, each organism having a maximum size less than or equal to 100 microns, for example less than or equal to 50 microns, and in particular between 5 microns and 20 microns.

Each microorganism is capable of causing an exothermic reaction involving the first chemical species C1.

Some microorganisms are capable for example of causing an oxidation exothermic reaction of the first chemical species C1. It is to be noted that exothermic reactions which are not redox reactions can also be contemplated.

The microorganism comprises at least one yeast for example. For example, the microorganism comprises a mixture of several different yeasts.

A yeast is a single-celled fungus.

In one specific embodiment, the yeast is Saccharomyces cerevisiae for example. It is to be noted that other types of yeasts can also be contemplated.

As a variant, the microorganism comprises at least one bacterium. For example, the microorganism comprises a mixture of several different bacteria.

Numerous types of bacteria can be contemplated for the microorganism.

For example, the microorganism comprises one type of commensal bacterium or a group (mixture) of several types of commensal bacteria. A commensal bacterium is a bacterium which colonises the body (generally the skin or mucosa) of a host such as a human being, without causing disease. The bacterium *Escherichia coli* is an example of a commensal bacterium which can be used in the invention.

When the implantable device 10 is intended to be implanted in the patient's intestine, the microorganism comprises at least one type of bacteria, for example which are naturally present in the intestine.

It is to be noted that other types of bacteria can also be contemplated,

The first exothermic reaction generates at least one product P via reaction of the first chemical species C1.

For example, the first exothermic reaction is a reaction between the first chemical species C1 and a second chemical species C2. An oxidation reaction is an example of reaction between the first chemical species C1 and the second chemical species C2. However, exothermic reactions which are not redox reactions can also be likely contemplated.

In one embodiment, the first exothermic reaction is a hydrolysis reaction of the first chemical species or of the second chemical species. In another embodiment, the first exothermic reaction is a disproportionation reaction of the first chemical species or of the second chemical species.

If the first chemical species C1 is glucose, the first reaction for example is decomposition of glucose in the presence of dioxygen, to a mixture of gluconic acid and hydrogen peroxide $H_2O_2$. In this case, the first exothermic reaction generates two products P which are gluconic acid and hydrogen peroxide.

If the element 80 comprises a group of bacteria, the first exothermic reaction is a metabolic reaction for example of the bacteria i.e. a reaction set in operation by the bacteria to stay alive, develop, reproduce or respond to stimuli of the environment to which the bacteria are exposed.

It is to be noted that a large number of first exothermic reactions can be contemplated, The second exothermic reaction is an exothermic reaction involving at least one product P generated by the first reaction. For example, the second exothermic reaction is a reaction between product P and a second chemical species C2.

In one embodiment, the second exothermic reaction is a reaction involving solely product P.

For example, the second exothermic reaction is a decomposition reaction of product P. One example of a decomposition reaction is the decomposition of hydrogen peroxide to a mixture of water and dihydrogen.

The element 80 is in contact for example with the hot end of at least one electrode 55, 60.

In the embodiment illustrated in FIG. 1, the element 80 surrounds the hot end of the corresponding electrode 55, 60. For example, the element 80 surrounds the hot end, here the first end 70, of each of the two electrodes 55, 60.

In particular, the element 80 surrounds the hot end of the corresponding electrode 55, 60 in a plane perpendicular to the main direction D. The element 80 is also interposed between the second casing 65 and the hot end, so that the hot end, the element 80 and the second casing 65 are aligned in this order along the main direction D.

The element 80 is a porous solid for example.

The element 80 is configured in particular so that molecules contained in the fluid F are able to pass therethrough.

In particular, the element 80 is designed so that the pores allow the passing of the first and/or second chemical species C1, C2.

A porous solid having pores of minimum size greater than or equal to 1 nanometre (nm) is an example of a porous solid able to be used as element 80.

The element 80 is formed for example of a thermal insulating material.

In particular, the element 80 is formed of a biocompatible material. Biocompatibility is the capacity of the materials not to interfere with, not to degrade the biological medium in which they are used. Biocompatible materials are also called biomaterials.

The element 80 has a thickness, measured in a direction perpendicular to the surface of the hot end, of between 1 micrometre and 2 centimetres.

The element 80 is a film for example at least partially covering the surface of the corresponding hot end.

As a variant, the element 80 is a block in contact with the hot end.

For example, the element 80 is an assembly of particles.

In one embodiment, the element 80 is a solid formed by compacting the particles.

In another embodiment, the thermo-electric generator 45 comprises a matrix, the particles being encapsulated in the matrix.

By "matrix", it is meant a binder ensuring cohesion between the different particles. In particular, a mass of matter surrounding each particle is an example of a matrix. For example, each particle is included in the matrix and is integral with the matrix.

For example, the matrix is a matrix formed of a polymer material.

In one embodiment, the element 80 is integrated in at least one semiconductor material forming the hot end of the corresponding electrode 55, 60. For example, the semiconductor material is porous and forms a matrix for the particles forming element 80.

The hot end of an electrode 55, 60, in which the semiconductor material is porous and forms a matrix for the particles, is formed for example by mechanically compacting semiconductor particles, in particular nanoparticles, and particles of the element 80. In one embodiment, the hot end is formed by mechanically compacting semiconductor particles, particles of the element 80 and polymer particles.

According to another embodiment that can be contemplated, the hot end is formed from an ink comprising semiconductor particles, particles of element 80 and polymer particles.

The second casing 65 is configured thermally to insulate at least one portion of the hot end of each electrode 55, 60 from the fluid F in which the thermo-electric generator 45 is immersed.

In particular, the second casing 65 delimits a chamber 85 containing at least the hot end of each electrode 55, 60.

The element 80 in particular is housed in the chamber 85.

In the example illustrated in FIG. 1, the cold end of each electrode 55, 60 is not housed in the chamber 85. In particular, the cold end of each electrode 55, 60 bathes in the fluid F.

It is to be noted that embodiments in which each electrode 55, 60 is fully housed in the chamber 85 can be contemplated. For example, the second casing 65 comprises an inner wall dividing the chamber 85 into two sub-chambers, the hot end of each electrode 55, 60 being housed in one sub-chamber and the cold end of each electrode 55, 60 being housed in the other sub-chamber. The inner wall is then configured to insulate the two sub-chambers thermally from each other.

In another embodiment, the chamber 85 is delimited by the second casing 65 and by a surface of an electrode 55, 60. In this case, the second casing 65 is secured for example to the electrode 55, 60 and configured to hold the corresponding element 80 in contact with the electrode 55, 60.

The second casing 65 is configured so that the first chemical species C1 is able to pass therethrough. For example, the second casing 65 comprises a pump capable of injecting a flow of fluid F into the chamber 85.

For example, the pump is a piezoelectric diaphragm pump.

As a variant, the second casing 65 is formed of a porous material through which the fluid F is able to pass.

In another variant, the second casing 65 is configured so that solely the first chemical species C1 is able to pass therethrough.

The second casing 65 is formed of a polymer material for example, in particular a porous polymer material through which the chemical species C1 and C2 are able to pass.

In the preceding example, the thermo-electric generator 45 is described in the event that the thermo-electric generator 45 is integrated in an implantable device 10. It is to be noted that embodiments in which the thermo-electric generator 45 is intended to be immersed in a fluid F which is not a body fluid can also be contemplated.

For example, the fluid F is a fluid discharged by an industrial or agricultural installation. In this case, the first chemical species C1 is selected for example from the group formed by urea, a sugar, an alcohol and biomass.

In one variant, the fluid F is a stream of wastewater such as mains drainage, in particular kitchen or sewage wastewater.

In this case, the first chemical species C1 is selected for example from the group formed by urea, a sugar and an alcohol.

The operation of the thermo-electric generator 45 will now be described with reference to FIG. 2.

Figure 2:
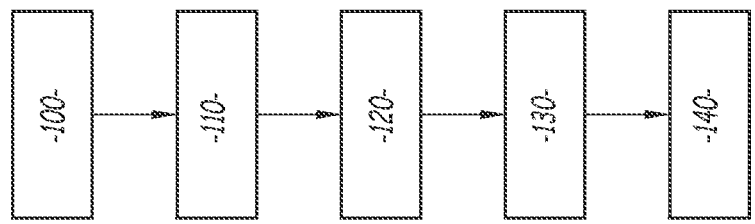
FIG. 2 is a flowchart of an example of a method for generating an electric potential difference implemented with the thermo-electric generator in FIG. 1.

A flowchart of the steps of an example of a method for generating a potential difference is illustrated in FIG. 2.

The generation method comprises a provision step 100, an immersion step 110, an implementation step 120, a temperature difference onset step 130 and an electric potential difference onset step 140.

At the provision step 100, a thermo-electric generator 45 is provided.

At the immersion step 110, the thermo-electric generator 45 is immersed in the fluid F.

For example, the implantable device 10 is implanted in the body and secured by means of the anchor 35 in a body cavity so that the thermo-electric generator 45 bathes in the fluid F filling the body cavity.

If the fluid F is not a body fluid, the thermo-electric generator 45 is secured in position so that it bathes in the fluid F, secured for example to an inner wall of piping intended to contain the fluid F.

At the implementation step 120, at least the first exothermic reaction is implemented by the element 80. For example, the fluid F comes into contact with the element 80 and the first exothermic reaction is caused by the element 80.

In particular, the element 80 causes the first and each second exothermic reaction. More specifically, the element 80 causes the first exothermic reaction, at least from the first chemical species, which leads to the onset of product P. The element 80 additionally causes the second exothermic reaction from product P generated by the first exothermic reaction.

It is to be noted that a large number of exothermic reactions are able to be used. For example, when the element 80 comprises a glucose oxidase and a catalase, a catalase, a fructose oxidase, a sucrase and a galactose oxidase, the element 80 causes oxidation of the glucose to gluconic acid and hydrogen peroxide, the hydrogen peroxide then being decomposed by means of the catalase.

When the element 80 comprises a glucose oxidase, a fructose oxidase, a sucrase and a galactose oxidase, the sucrose is decomposed by the sucrase to glucose, fructose and galactose, these products then being themselves decomposed by the glucose oxidase, fructose oxidase and galactose oxidase.

At the temperature difference onset step 130, a temperature difference occurs subsequent to the exothermic reaction(s) between the hot end and cold end of each electrode 55, 60 comprising an element 80. More specifically, the exothermic reaction(s) lead to heating of the hot end in relation to the cold end.

At the potential difference onset step 140, an electric potential difference occurs between the two second ends 75 subsequent to the onset of the temperature difference, via thermoelectric effect.

In particular, an electric voltage is produced between the hot and cold ends of each electrode 55, 60 comprising an element 80. Since the two first ends 70 are electrically connected to each other, a potential difference is thereby generated between the two second ends 75.

The potential difference for example is between 1 microvolt per degree Kelvin and 9 millivolts per degree Kelvin.

The potential difference is transmitted to the converter 30, for example via two electric conductors each connecting the convertor 30 to the second end 75 of an electrode 55, 60.

Through the use of the element 80, the thermo-electric generator 45 is able to generate a potential difference even when the thermo-electric generator 45 is immersed in a fluid F of homogeneous temperature. For example, when the thermo-electric generator 45 is implanted in the body, the thermo-electric generator 45 is able to deliver electric power in the region of several milliwatts even though body temperature is relatively homogeneous. Similarly, the thermo-electric generator 45 is able to generate significant electric power when immersed in an outflow discharged from an industrial installation even though this outflow is of homogeneous temperature.

The thermo-electric generator 45 is therefore able to deliver significant electric power even when the thermo-electric generator 45 is in a medium in which a prior art thermo-electric generator would only produce little or no electric power.

In addition, the thermo-electric generator 45 is not restricted to media in which oxidants and reducing agents are present, but can be used in a large number of media provided that chemical species are available that are capable of reacting together to form an exothermic reaction, even if this reaction is not a redox reaction.

The thermo-electric generator 45 is therefore adapted to a greater number of media than thermo-electric generators 45 in the state of the art.

Additionally, the thermo-electric generator 45 is of small size and is therefore better adapted than other types of electric generators for applications such as the electric powering of implantable devices.

The second casing 65 allows thermal insulation of the hot end from most of the fluid, and therefore allows easy reaching of temperatures at the hot end that are greater than would be reached without a second casing 65. The generated electric power is therefore greater than that generated without a second casing 65.

Polymer materials are particularly suitable for forming the thermally insulating second casings 65. Also, numerous polymers are particularly well tolerated by a human or animal body.

A second casing 65 formed of a porous material allows the combining of both thermal insulation and ease of operation since no pump is required. In addition, the available electric power output from the thermo-electric generator is greater, since no electric power is diverted to feed a pump.

The use of a pump to inject the fluid F into the chamber 85 allows an increase in the flow rate of fluid F which comes into contact with the element 80, compared with the case in which movement of the fluid F takes place solely via convection. Also, the flow rate of fluid F, and hence the electric power generated by the implantable device 10, is able to be adjusted by controlling the pump.

A piezoelectric diaphragm pump consumes little energy and is very well adapted for applications in which the volume of fluid F injected into the chamber 85 is small, for example when the thermo-electric generator 45 is implanted in the body.

If the element 80 is in the form of particles dispersed in a matrix, or a porous solid formed of compacted particles, a large number of chemical species C1, C2 are able to come into contact with the element 80 and therefore to take part in the corresponding exothermic reaction. Here again, the generated electric power is greater.

Since bacteria and yeasts are able to self-reproduce, the performance of the thermo-electric generator 45 over time is less likely to decrease than with other types of elements 80.

Yeasts and bacteria also have good resistance to the environment in which they are immersed, in particular if these species are naturally present in the environment in which the implantable device 10 is intended to be immersed, particularly if these species are naturally present in the fluid F. This is the case for example for intestinal bacteria when the implantable device 10 is intended to be implanted in the intestine.

Enzymes display high selectivity in the catalysed reactions and therefore provide good control over these reactions.

The use of at least two successive exothermic reactions, one involving the products P of the other, allows an increase in the temperature obtained at the hot end and therefore an increase in the delivered electric power.

Glucose is a molecule available in numerous body fluids F and is therefore well adapted for use as first chemical species C1 and/or second chemical species C2, especially as numerous exothermic reactions involve glucose and/or the products P resulting from decomposition thereof.

In the above example, the thermo-electric generator 45 has been described for the case in which the thermo-electric generator 45 comprises two electrodes 55, 60. It is to be noted that embodiments in which the thermo-electric generator 45 comprises more than two electrodes 55, 60 can be contemplated.

For example, the thermo-electric generator 45 comprises three electrodes mounted in series so that the second end 75 of the second electrode 60 is electrically connected to the second end 75 of a third electrode. The third electrode, in particular, is identical to the first electrode 55.

The potential difference thus generated by the thermo-electric generator 45 is measured between the second end 75 of the first electrode 55 and the first end 70 of the third electrode. In particular, a first potential difference occurs between the second ends 75 of the first electrode 55 and of the second electrode 60, and a second potential difference occurs between the first end and the second end of the third electrode.

Embodiments in which more than three electrodes are mounted in series in the thermo-electric generator 45 can also be contemplated.

Figure 3:
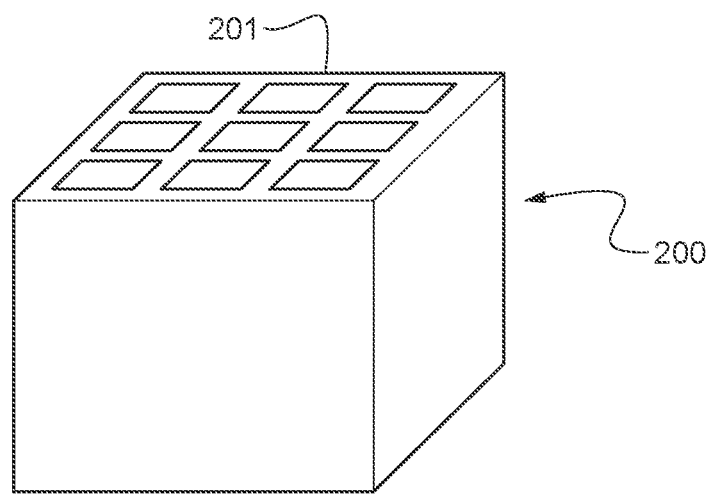
FIG. 3 illustrates a porous 3D matrix of a thermo-electric generator according to one embodiment of the present invention.

Referring to FIG. 3, it can be seen that a porous 3D matrix 200 is illustrated, which can be used as porous material for a thermo-electric generator of the present invention.

The porous 3D matrix 200 in the illustrated embodiment is cubic, the invention not being restricted however in this respect, the porous 3D matrix possibly also having a cylindrical or slab shape.

The rectangles 201 shown on the porous 3D matrix 200 represent the pores of the porous 3D matrix 200. The size of the pores of the porous 3D matrix can vary from 50 µm up to 1 mm.

The porous 3D matrix is fabricated for example via 3D printing from a viscous paste of metal particle powder and a viscous binder, the particles of the metal particle powder for example being carbon particles carbon nanotube particles, activated carbon particles, graphene particles, aluminium particles.

The viscous binder is an element or mixture of several elements from among the following compounds: cellulose derivatives, alginate, agarose, polyvinyl alcohol, polyvinyl chloride.

A face of the porous 3D matrix 200 is closed by a thermal insulator e.g. PCB, the other faces of the porous 3D matrix being closed by a heat-conducting material, e.g. aluminium.

The bacteria or microorganisms will be able to grow inside the pores 201 of the porous 3D matrix 200.

Figure 4:
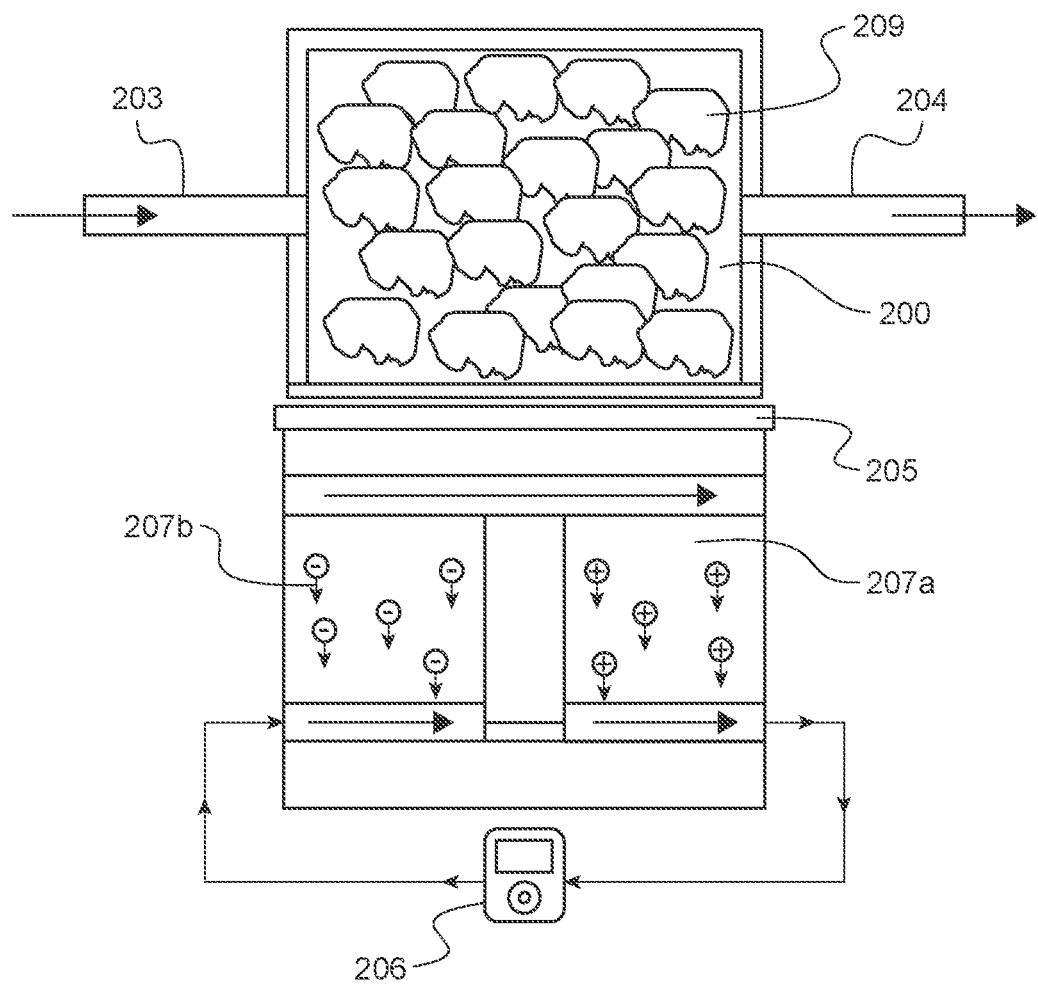
FIG. 4 illustrates a thermo-electric generator according to one embodiment of the present invention.

FIG. 4 illustrates a thermo-electric generator 202 according to one embodiment of the present invention in use with a porous 3D matrix 200 shown in FIG. 3.

As can be seen in FIG. 4, the porous 3D matrix 200 comprises a fluid inlet 203, a fluid outlet 204, the fluid here being glucose to set up a glucose channel between the fluid inlet 203 and fluid outlet 204 to feed the bacteria or microorganisms contained therein, the porosity of the material forming the porous 3D matrix also allowing the feeding thereof.

The porous 3D matrix 200 is a carbon polymer matrix of low heat capacity so that heat losses are minimal in the thermoelectric generator 202, to optimise the heat released by the bacteria or microorganisms 209 contained therein. The porous 3D matrix is cubic in the illustrated nonlimiting embodiment, and five of its faces are coated with a thermal insulator, e.g. a polymer of parylene type, and the last face 205 is coated with a heat-conducting material of aluminium type for example.

The thermo-electric generator 202 is composed of a voltage source 206, two electrodes 207a and 207b of which one end is connected to the voltage source, and the other end is connected to a plate 208 in material of heat-conducting type, of aluminium type, to create a cold source on the side of the voltage source 206 and a hot source on the side of the plate 208. The plate 208 as hot source is put in contact with or in the vicinity of the face 205 of the porous 3D matrix 200 to transmit heat thereto.

Bacteria or microorganisms 209 are present in the porous 3D matrix 200. The use of the porous 3D matrix allows an increase in the number or density of bacteria or microorganisms 209 through the creation of bacterial or microorganism biofilms on the surface of and inside the porous 3D matrix 200.

The density of bacteria or microorganisms 209 is greater in a biofilm than when the bacteria or microorganisms are in solution.

The porosity of the 3D matrix also advantageously allows feeding of the microorganisms with water and substrates

The invention claimed is:

1. A thermo-electric generator intended to be immersed in a fluid containing at least one first chemical species, the thermo-electric generator comprising at least two electrodes, each electrode having a first end and a second end, the first ends being electrically connected to each other, the generator being configured to generate an electric potential difference between the two second ends when a temperature difference is imposed between each first end and the second end of the same electrode, the temperature difference being such that one end, called "hot end", among the first end and second end of each electrode has a temperature strictly greater than the temperature of the other end, called "cold end", among the first end and second end of the same electrode,
the hot end of at least one electrode comprising at least one element selected from the group formed by a microorganism and an enzyme, the element being capable of causing at least one exothermic reaction involving the first chemical species,
wherein the thermo-electric generator further comprises a block in contact with the hot end of at least one electrode, the block comprising a matrix, the matrix being formed in particular of a polymer material, the element being in the form of particles encapsulated in the matrix.

2. The thermo-electric generator according to claim 1, comprising a casing delimiting a chamber housing the two hot ends, the chamber also housing the element, the casing being configured so that at least the first chemical species is able to pass therethrough.

3. The thermo-electric generator according to claim 2, wherein the casing is formed of a porous material.

4. The thermo-electric generator according to claim 2, comprising a pump capable of injecting a flow of fluid from outside the casing to inside the chamber.

5. The thermo-electric generator according to claim 2, wherein the casing is formed of a polymer material.

6. The thermo-electric generator according to claim 3, wherein the porous material is made of a porous 3D matrix.

7. The thermo-electric generator according to claim 6, wherein the geometric shape of the matrix is one from among a cube, a cylinder, a slab.

8. The thermo-electric generator according to claim 6, wherein 70% to 80% of the surface of the 3D matrix is coated with a thermal insulation layer.

9. The thermo-electric generator according to claim 6, wherein the matrix has a fluid inlet and a fluid outlet.

10. The thermo-electric generator according to claim 6, wherein the 3D matrix comprises microorganisms which form a biofilm inside the 3D matrix.

11. The thermo-electric generator according to claim 6, wherein the porous matrix is a metal block.

12. The thermo-electric generator according to claim 1, wherein the element is able to cause a first exothermic reaction and a second exothermic reaction, the first reaction generating at least one product by reaction of the first chemical species, the second reaction being a reaction involving the product of the first reaction.

13. The thermo-electric generator according to claim 1, wherein at least one element is a microorganism, at least one of the following properties being verified:
the microorganism comprises a yeast, and
the microorganism comprises a bacterium.

14. The thermo-electric generator according to claim 1, wherein the first chemical species is selected from the group formed by: urea, an alcohol and a sugar.

15. The thermo-electric generator according to claim 14, wherein at least one species is glucose.

16. An implantable device configured to be implanted in a human or animal body, comprising a thermo-electric generator according to claim 1, wherein the fluid is a body fluid of the human or animal body, the first chemical species particularly being glucose.

17. The implantable device according to claim 16, wherein at least one element comprises an enzyme, the element comprising a glucose oxidase and a catalase.

18. The implantable device according to claim 16, wherein the implantable device is a pacemaker.

19. A method for generating an electric potential difference, comprising steps of:
providing a thermo-electric generator comprising at least two electrodes, each electrode having a first end and a second end, the first ends being electrically connected to each other, the generator being configured to generate an electric potential difference between the two second ends when a temperature difference is imposed between each first end and the second end of the same electrode, the temperature difference being such that one end called "hot end" among the first end and the second end of each electrode has a temperature strictly greater than the temperature of the other end, called "cold end", among the first end and the second end of the same electrode, the hot end of at least one electrode comprising at least one element selected from the group formed by a microorganism and an enzyme, the thermo-electric generator-further comprising a block in contact with the hot end of at least one electrode, the block comprising a matrix, the matrix being formed in particular of a polymer material, the element being in the form of particles encapsulated in the matrix,
immersing the thermo-electric generator in a fluid comprising at least one first chemical species,
implementing, by the element, at least one exothermic reaction involving the first chemical species,
onset of a temperature difference between the hot end and the cold end of the electrode comprising the element, and
onset of an electric potential difference between the two second ends.

* * * * *